United States Patent [19]

Sciaraffa et al.

[11] 4,381,781
[45] May 3, 1983

[54] FLEXIBLE WAIST DIAPER

[75] Inventors: Michael A. Sciaraffa, Outagamie County; Leona G. Boland, Winnebago County, both of Wis.

[73] Assignee: Kimberly-Clark Corporation, Neenah, Wis.

[21] Appl. No.: 222,359

[22] Filed: Jan. 5, 1981

[51] Int. Cl.³ .............................................. A41B 13/02
[52] U.S. Cl. .................................... 604/372; 604/373; 604/375; 604/385; 604/390
[58] Field of Search ................. 128/284, 286, 287, 288

[56] References Cited

U.S. PATENT DOCUMENTS

| | | | |
|---|---|---|---|
| 3,860,003 | 1/1975 | Buell | 128/287 |
| 3,995,638 | 12/1976 | Schaar | 128/284 |
| 4,182,334 | 1/1980 | Johnson | 128/284 |
| 4,205,679 | 6/1980 | Repke et al. | 128/287 |
| 4,210,143 | 7/1980 | De Jonckheere | 128/287 |

*Primary Examiner*—C. Fred Rosenbaum
*Attorney, Agent, or Firm*—Richard C. Ruppin; William D. Herrick

[57] ABSTRACT

An elasticized waist diaper in which a layer of elastic material is positioned in an opening in the waist area of a diaper. The elastic layer is located such that it forms a portion of the waist edge of the diaper. The elastic layer may be formed from the same piece of elastic material as is used for the diaper leg elastic.

20 Claims, 7 Drawing Figures

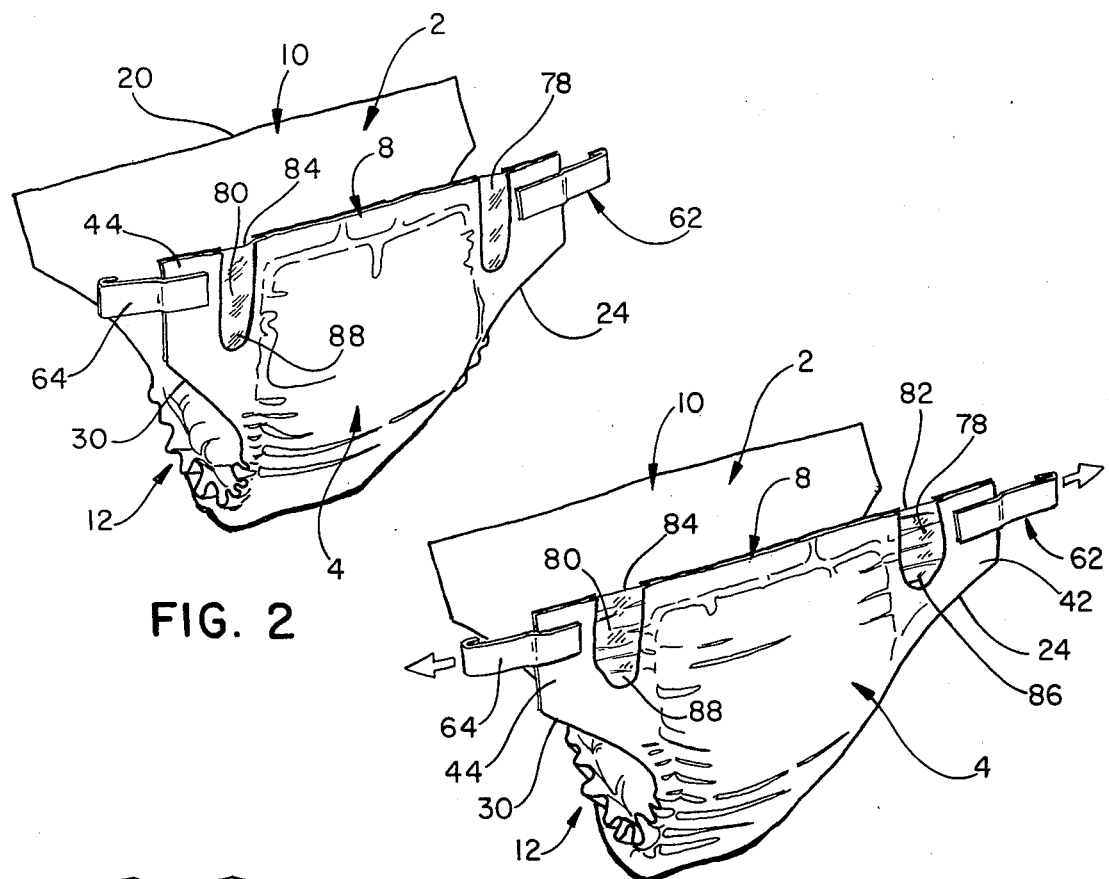
FIG. 2
FIG. 3
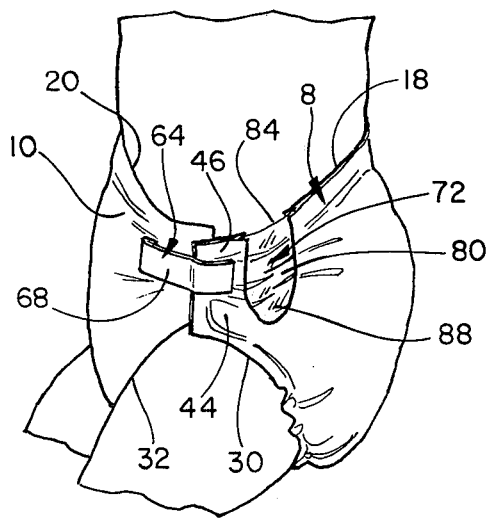
FIG. 4
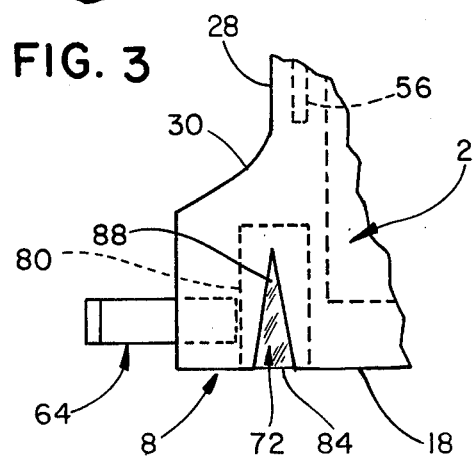
FIG. 5
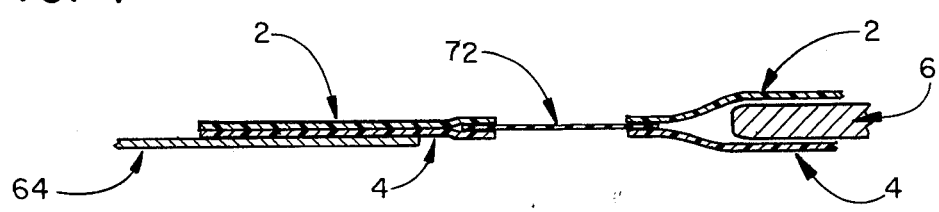
FIG. 7

FLEXIBLE WAIST DIAPER

BACKGROUND OF THE INVENTION

The present invention relates to disposable diapers and more particularly to a stretchable waistband for a disposable diaper.

Diapers of the disposable type have, during recent years, come into widespread use. Their increased popularity can be attributed to their elimination of the inconvenience of having to wash diapers, their ease of use, particularly when removing a soiled diaper from an infant, and the dryer comfort they provide due to the use of improved materials relative to conventional reusable diapers.

While the use of disposable diapers has greatly increased due to their various advantages over reusable diapers, they continue to have several defects necessitating continued work toward their improvement. One of these defects is urine leakage in the waist area of the diaper. A wide variety of diaper elastic waist constructions have been developed in attempts to remedy the problem. However none of these have been satisfactory to the point of enjoying any significant commercial success. Typical drawbacks are complexity of the construction or adding of excessive components which make the diaper difficult to manufacture and add unacceptable material costs, a construction which is inherently difficult to manufacture, lack of durability of the construction, insufficient elasticity either entirely or in the area of the waist where it is most needed, and lack of aesthetic appeal. For example, an elastic waist construction is disclosed in Schaar U.S. Pat. No. 3,995,640 in which an elastic strip or strips or an elastic loop is placed transversely in the waist area of the diaper. In the case of elasticization using the strip, the folding of the diaper waist end, which must take place after the continuous web is cut into individual diapers, is extremely difficult to accomplish. This is because the leg elastic will retract the individual diaper lengthwise if it is not held entirely flat while moving rapidly along the production line until packaging and the folding operation while simultaneously holding the diaper flat cannot be done readily. This problem is also true of the elastic loops and, moreover, the arranging of the loops is far too intricate to permit their attachment to diapers during high speed production.

In Kozak U.S. Pat. No. 4,036,233, an example of an elastic waist construction is disclosed in which the necessary elasticity is actually lacking. A topsheet and backsheet are provided and one of the two sheets comprises a material which is stretchable relative to the other sheet. The two sheets are bonded together in the waistband area. Since the stretchable sheet is intended to provide stretch to the waist area, the nonstretchable sheet is provided with slits or openings so that it does not prevent movement of the stretchable sheet. The two sheets, however, remain bonded together along the edge of the waist and the slits do not extend to any significant degree beyond the area of stretching tension applied to the waist. Thus, in fact, almost all waist tension will be nevertheless carried by the nonstretchable material and very little waist stretch will occur.

In Jacob U.S. Pat. No. 3,800,796, an elasticized waist is provided by means of a fastening tape incorporating a stretchable mid-portion. The problem with this construction is that the flexibility of the tape permits excessive pivoting movement of the diaper side waist portions during movement by the wearer. The result is skewing of the side waist portions and deterioration of the waist fit to cause increased urine leakage problems.

SUMMARY OF THE INVENTION

A principal object of the present invention is to provide a diaper waist construction which improves fit and minimizes leakage at the waist.

Another object of the invention is to provide a diaper waist construction having a substantial elastic capability.

Another object of the invention is to provide an elasticized diaper waist construction which can be easily manufactured.

A further object of the invention is to provide a highly durable elasticized diaper waist.

A still further object of the invention is to provide an aesthetically appealing elasticized diaper waist.

The objects of the invention are accomplished by placing, in the waist area of the diaper, a layer of film of elastic material which extends into the diaper from its waist edge. Since there is no relatively non-elastic material between the waist edge and the elastic layer, the stretch of the elastic layer will not be constrained by the non-elastic material and good waist fit will result. Moreover, extending the elastic layer into the diaper in the longitudinal direction of the diaper, beyond the area of tension applied transversely to the diaper at the waist, substantially avoids constraint of the waist stretch due to the non-elastic material adjacent the inward end of the elastic material. The attaching of the elastic material to the back sheet and/or top sheet of the diaper requires only cutting the sheets as they move in web form, cutting the elastic material, and pressing the elastic material against one of the sheets. These manufacturing steps are all readily accomplished in conjunction with the usual high speed diaper production lines. Moreover, the addition of elastic material requires no fabrication of any separate components to add to the diaper other than the elastic piece itself.

DESCRIPTION OF THE DRAWINGS

The present invention will be further illustrated by reference to the following description of the invention taken in conjunction with the following drawings wherein:

FIG. 2 is a perspective view of the diaper of FIG. 1 illustrating the waist area in an unstretched condition;

FIG. 3 is a perspective view of the diaper of FIG. 2 illustrating the waist area in a stretched condition;

FIG. 4 is a perspective view of the diaper of FIG. 2 illustrating the waist area in a stretched condition when the diaper is fastened at a wearer's waist.

FIG. 5 is a partial plan view of another embodiment of the disposable diaper in a flat condition;

FIG. 7 is a cross-sectional view of the waist area of the diaper taken along plane 7—7 of FIG. 1.

DETAILED DESCRIPTION OF THE PREFERRED EMBODIMENT

Figure 1:
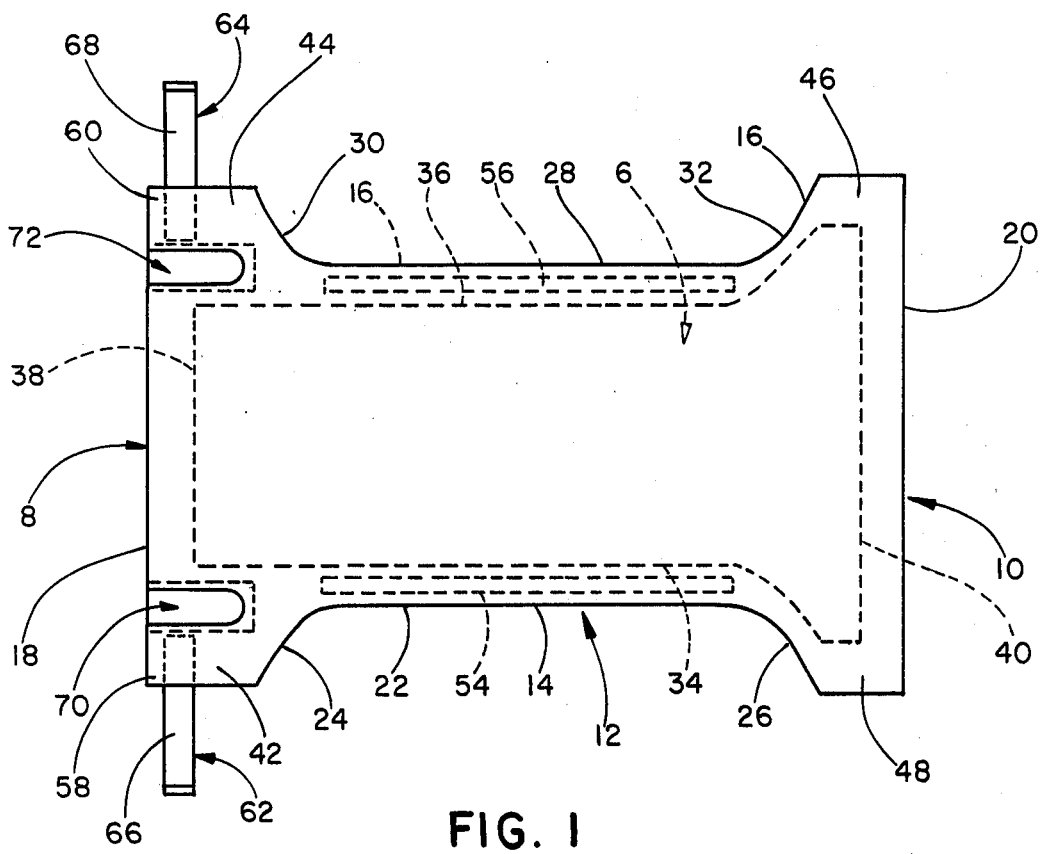
FIG. 1 is a plan view of one embodiment of the disposable diaper in a flat condition.

Referring now to the drawings, there is shown a disposable diaper having a topsheet 2, a backsheet 4, and an absorbent pad 6 disposed substantially centrally between the topsheet and backsheet. The absorbent pad 6 may be adhered or otherwise bonded to the topsheet or backsheet or both.

The backsheet 4 comprises a thin, flexible liquid impermeable material, preferably an olefinic or vinyl film. A low density polyethylene having a thickness of from about 0.4 to about 1.5 mils is typical, although a thickness of about 1 mil is preferred. The topsheet 2 is in contact with the body during wearing of the diaper and comprises a liquid permeable material such as a bonded-carded non-woven web of fibers. The absorbent pad 6 comprises a liquid absorbent material such as wood pulp fluff.

The diaper has a longitudinal or length dimension and front and rear waist areas positioned at either end of its length and respectively identified by the numbers 8 and 10. The diaper also has a width dimension in a direction transverse to the longitudinal dimension of the diaper. The waist areas 8 and 10 respectively have edges 18 and 20 running in the transverse direction of the diaper and, in the embodiments illustrated in the drawings have a length equal to the maximum width of the diaper. A leg area 12 is positioned intermediate the waist areas 8 and 10. The length of the diaper has side edges 14 and 16 running along the leg area 12 and waist area 8 and 10. The side edge 14 includes an edge portion 22 along one side of the leg area 12 and edge portions 24 and 26 respectively adjacent the waist areas 8 and 10. The side edge 16 includes an edge portion 28 along the leg area 12 and edge portions 30 and 32 respectively adjacent the waist areas 8 and 10.

Figure 6:
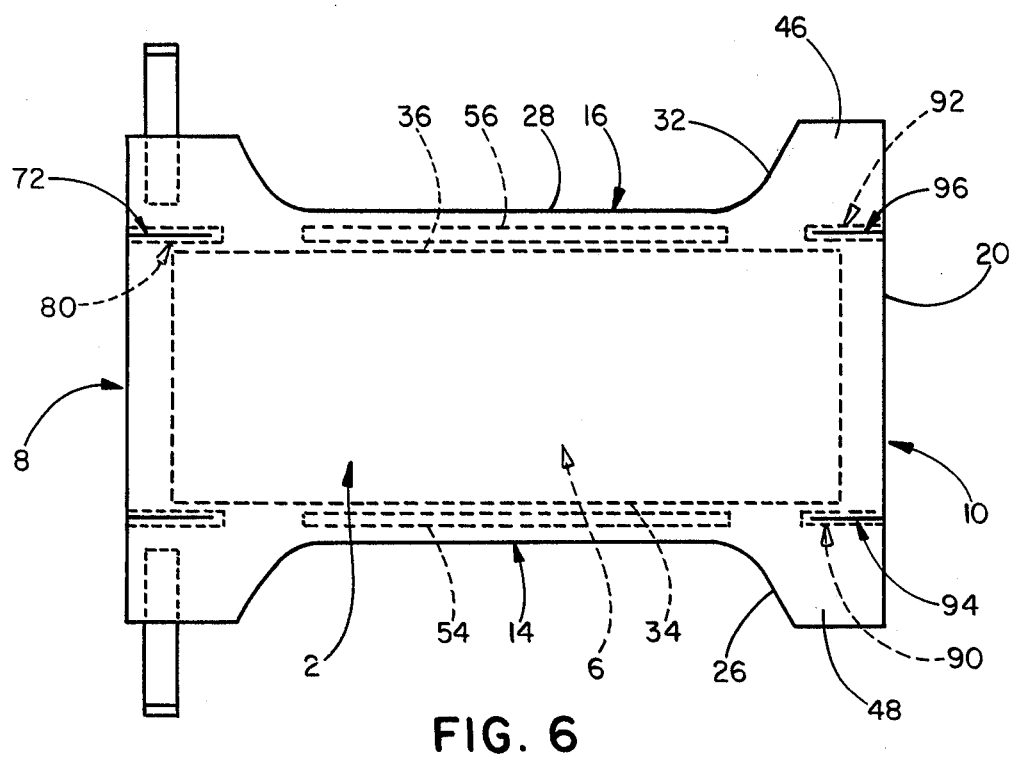
FIG. 6 is a plan view of another embodiment of the disposable diaper also in a flat condition.

The diaper also includes, at its opposite ends, ears 42, 44, 46 and 48 extending in a lateral direction, that is, transversely of the length of the diaper. As may be seen in the drawings the diaper side edge portions 24, 30, 32 and 26 respectively also form edges of ears 42, 44, 46 and 48. The absorbent pad 6 may have a variable width, for example, where it has ears 50 and 52 as shown in the embodiment of FIG. 1. The pad 6 also includes end edges 38 and 40 and side edges 34 and 36, the latter defining the variable width of the pad 6. In view of the spacing of the edges 34, 36, 38 and 40 of the absorbent pad 6 from the corresponding diaper edges 22, 18, 28 and 20, the marginal areas of the topsheet 2 and backsheet 4 are engagement with each other. To contain the absorbent pad 6 and provide integrity to the diaper, the topsheet 2 and backsheet 4 are joined to each other by suitable means such as an adhesive in these areas. Elastic strips 54 and 56 comprising natural rubber or a synthetic elastomeric such as "Tuftane", a polyurethane elastomer marketed by the B. F. Goodrich Company, are attached to the diaper in the leg area 12 between the edges 34 and 36 of the absorbent pad 6 and the diaper edges 14 and 16. The strips 54 and 56 are in a stretched condition extending parallel to the length of the diaper when the latter is laid flat as shown in FIGS. 1, 5 and 6. When the diaper is not held flat and is in a position as shown in FIGS. 2 and 3, the strips 54 and 56 relax and contract and cause the diaper topsheet 2 and backsheet 4 to pleat in a somewhat random fashion. In FIG. 4, when the diaper is being worn, the strips 54 and 56 are in a partially contracted condition in which they apply sealing pressure to the leg of the wearer. The elastic strips 54 and 56 are bonded to the backsheet 4 by suitable means such as an adhesive usually applied to the strips. Disposed at and attached to each of the corners 58 and 60 of the waist area are fastening tapes 62 and 64 each having a coating of a pressure-sensitive adhesive on their faces 66 and 68. When the diaper is being worn, as shown in FIG. 4, the faces 66 and 68 of the tapes are pressed against and releaseably adhered to the waist area 10 to hold the diaper in place.

With reference to FIG. 1, the waist area 8 includes openings 70 and 72 through the joined topsheet 2 and backsheet 4. The openings 70 and 72 intersect the waist edge 18 such that there is no diaper material between each of the openings 70 and 72 and the waist edge 18. Stated another way, the openings 70 and 72 are positioned such that the joined topsheet 2 and backsheet 4 are caused to be discontinuous along the waist edge 18. The opening 70 is defined by the edge 74 and the opening 72 is defined by the edge 76. Elastic layer material such as layers 78 and 80 is respectively disposed in the openings 70 and 72 and affixed to either the topsheet 2 or backsheet 4, or both, so that the layers 78 and 80 become an integral part of the diaper as shown in FIG. 7. During manufacture of the diaper, the elastic layers 78 and 80 are applied to the diaper in a relaxed condition. Thus, the problems of stretching the elastic prior to application to the diaper and maintaining the elastic stretched during such application, while completing the fabrication of the diaper and packaging it, are eliminated. The layers 78 and 80 respectively include edges 82 and 84 comprising a portion of the waist edge 18. The layers 78 and 80 also respectively include ends 86 and 88 spaced from their waist edge portions 82 and 84. The elastic layer material may be a material such as "Tuftane", previously mentioned with regard to elastic strips 54 and 56, or any of several other types of elastomeric films producible in thicknesses of 0.25 to 10.0 mils with a preferred thickness of 1.5 mils and having the necessary tensile strength and modulus of elasticity. The tensile strength may be approximately 6,000 psi (ASTM D-382-61T) and the modulus of elasticity less than 5,000 psi at 100% elongation (ASTM D-882-61T).

The elastic layers 78 and 80 are preferably, although not necessarily, disposed laterally outward of the most adjacent portions of the pad 6 side edges 34 and 36 as shown in FIG. 1. Also, the elastic layers 78 and 80 may respectively be located entirely or partially within the ears 42 and 44 or entirely laterally inward of the ears 42 and 44. The waist tapes 62 and 64 are respectively preferably located closer to the waist edge portions 82 and 84 of the elastic layers 78 and 80 than to the ends 86 and 88.

Referring now to FIGS. 1-4, the waist tapes 62 and 64 are shown in FIGS. 1 and 2 in an extended position and the elastic layers 70 and 72 are in a relaxed condition. In FIG. 2, the diaper is substantially in the position it occupies while being fitted to a wearer just prior to fastening the front and rear waist areas 8 and 10 together. In FIG. 3, the position of the diaper is similar to that of FIG. 2 except that the waist tapes 62 and 64 have been pulled, i.e. tensile force has been applied laterally of the diaper length, in the direction of the arrows. In FIG. 4, the diaper is shown completely fitted on a wearer with the tape 64 under tension and fastening the front and rear waist areas 8 and 10 together. Only elastic layer 80 is shown in FIG. 4 and only its function in association with other components of the diaper need by discussed inasmuch as the function of the two elastic layers 78 and 80 is the same. When the waist tape 64 is either pulled as shown in FIG. 3 or fastened along the waist of the wearer to connect the waist areas 8 and 10 together, the waist area 8 and the elastic layer 80 are placed in a tensile stressed condition in a direction transverse to the length of the diaper. The tensile stress is maximum in the immediate vicinity of the waist area 8 in alignment with the direction of stress on the tape 64 and decreases with increasing distance from the tape 64 in a direction parallel to the length of the diaper. Due to the inelasticity of the topsheet 2 and backsheet 4, or both, most of the transverse tensile stress is applied to the elastic layer 80 causing it to stretch and provide a snug fit between the skin of the wearer and the waist areas 8 and 10. Since the waist edge portion 84 is formed entirely of elastic layer 80, there will be substantially no limitation on the extension of the layer 80 and consequently the snugness of the fit along the waist area 8, by other nonelastic materials. Moreover, the elastic layer 80 extends preferably sufficiently far in a direction parallel to the length of the diaper toward the leg area 12 to substantially eliminate restraint to the stretching of the layer 80 by the topsheet 2 or backsheet 4. In addition, the length of the layer 80 away from the location of the application of transverse tension by the tape 64 to the waist area 8, is such that at least a portion of the ear 44 will pivot to some extent about the area of the diaper between the end 88 of the layer 80 and the waist side edge portion 30. This mode of functioning is, of course, made possible by the relatively free extensibility of the elastic layer 80 along its waist edge 84. On the other hand, due to the position of the elastic layer 80 in the waist area 8 of the diaper, the overall rigidity of the diaper when being worn as illustrated in FIG. 4 prevents movement of the waist areas 8 and 10 relative to each other and consequent loosening of the waist.

In FIG. 5 is shown an embodiment of the invention in which the opening 72 has a "V" shape in which the width of the opening and the effective stretchable portion of elastic layer 80 decreases with increasing distance from the waist area edge 18. The advantage of this construction is that, while the benefits of the embodiment of FIG. 1 are substantially retained, at the same time the elastic layer 80 occupies less of the diaper surface area so that greater rigidity and ruggedness results.

In another embodiment of the invention, shown in FIG. 6, the opening 72 may have a very small width, preferably being only a slit through the topsheet 2 and backsheet 4. Openings 94 and 96 and elastic layers 90 and 92 are disposed in the waist area 10. As in the embodiment shown in FIG. 1, essentially only elastic layer 80 and its associated parts of the diaper need be described. The elastic layer 80 also has a relatively small width and the length of the elastic layer 80 as well as the length of the opening 72 are aligned with the length of the elastic strip 56. Moreover, the elastic layer 80 and the elastic strip 56 may be provided from the same continuous piece of ribbon of elastic material during the manufacture of the diaper. The elastic ribbon may either be cut or may be continuous through the leg area 28 and waist areas 8 and 10 to form the elastic strip 56 and elastic layers 80 and 92. However, as previously mentioned, the elastic strip 56 is affixed to the topsheet 2 or backsheet 4, or both, in a stretched condition while the elastic layer 80 is affixed to the sheets in an unstretched condition.

In view of the foregoing description, it may be appreciated that an elasticized waist diaper has been provided which gives a snug waist fit to thereby prevent leakage of fluid from within the diaper, is relatively easy to manufacture, and otherwise fulfills the objectives earlier stated.

It will be understood that the foregoing description of the present invention is for purposes of illustration only and that the invention is susceptible of a number of modifications or changes, none of which entail any departure from the spirit and scope of the present invention as defined in the hereto appended claims.

What is claimed is:

1. In a disposable diaper having a liquid permeable top sheet for placement adjacent a body, a liquid impermeable backsheet joined to said topsheet, an absorbent pad disposed between said sheets, front and rear waist area at opposite ends of the diaper, a pair of side edges extending the length of the diaper, front and rear waist edges formed by the joined sheets and extending the width of the diaper, and fastening means secured to one of said waist areas for connecting the front and rear waist areas together, the improvement wherein a waist area includes an opening in both of the joined sheets, said opening intersecting a waist edge, and an elastic layer disposed in said opening and forming a part of said waist edge, said elastic layer being joined to at least one of said sheets whereby the waist area may be effectively stretched and tightened when tension is applied to the waist area by the fastening means during connection of the front and rear waist areas.

2. The diaper according to claim 1 wherein said absorbent pad has two side edges defining a variable pad width and at least a portion of said elastic layer is positioned laterally outside of the space between two planes parallel to the length of the diaper and respectively passing through a different one of said pad side edges at any point along the length of the side edge.

3. The diaper according to claim 1 wherein said elastic layer is positioned laterally of the absorbent pad.

4. The diaper according to claim 1 wherein only the elastic layer forms the waist edge in the area of the opening.

5. The diaper according to claim 1 wherein said diaper has at least one laterally extending ear at an end of the diaper and said elastic layer is positioned in said ear.

6. The diaper according to claim 5 wherein said elastic layer is positioned laterally of the absorbent pad.

7. The diaper according to claims 5 or 6 wherein said ear has an edge running at least partially in a lateral direction relative to the length of the diaper and comprising a portion of the side edge of the diaper, said ear being pivotally movable about the area of the ear positioned between the elastic layer and said ear edge.

8. The diaper according to claims 5 or 6 wherein the absorbent pad extends into an ear at one end of the diaper and does not extend into an ear at the opposite end of the diaper.

9. The diaper according to claims 1, 5 or 6 wherein at least one of said sheets is non-elastic relative to said elastic layer, the elastic layer has an end spaced from the waist edge partially formed by such elastic layer, and a portion of said joined sheets positioned between a side edge of the diaper and the elastic layer is pivotally movable about the area of the diaper adjacent to the end of the elastic layer.

10. The diaper according to claims 1, 5 or 6 wherein said diaper further comprises a leg area intermediate said waist areas, an elastic strip in each leg area adjacent a side edge and extending in the direction of the length of the diaper, said elastic layer being positioned substantially in alignment with the direction of the elastic strip most adjacent the elastic layer.

11. The diaper according to claims 1, 5 or 6 wherein a strip of elastic material is positioned along at least a portion of one of said side edges intermediate said waist areas, and said elastic layer and elastic strip comprise the same piece of elastic material.

12. The diaper according to claims 1, 5 or 6 wherein at least one of said sheets is non-elastic relative to said elastic layer, said waist area being in a tensile stressed condition due to the connection of the front and rear waist area together, said tensile stress decreasing with increasing distance from the waist edge in the direction of the length of the diaper, and the elastic layer has a sufficient length parallel to the length of the diaper beyond the area of application to such tensile stress to eliminate any restraint to the stretching of the elastic layer by the non-elastic sheet.

13. The diaper according to claim 12 wherein said diaper further comprises a leg area intermediate said waist areas, an elastic strip in each leg area adjacent a side edge and extending in the direction of the length of the diaper, said elastic layer being positioned substantially in alignment with the direction of the elastic strip most adjacent the elastic layer.

14. The diaper according to claim 12 wherein the elastic layer has a width less than its length.

15. The diaper according to claim 14 wherein the width of the elastic layer decreases with increasing distance from the waist edge partially formed by the elastic layer.

16. The diaper according to claim 12 wherein the elastic layer has an end spaced from the waist edge partially formed by such elastic layer and the portion of said joined sheets positioned between a side edge of the diaper and the elastic layer are pivotally movable about the area of the diaper adjacent to the end of the elastic layer.

17. The diaper according to claim 12 wherein the diaper has at least one laterally extending ear at an end of the diaper, said ear having an edge running at least partially in a lateral direction relative to the length of the diaper and comprising a portion of the side edge of the diaper, the elastic layer being positioned in said ear, said ear being pivotally movable about the area of the ear between the elastic layer and the lateral ear edge.

18. The diaper according to claim 17 wherein the absorbent pad extends into an ear at one end of the diaper and does not extend into an ear at the opposite end of the diaper.

19. In a disposable diaper having a liquid permeable top sheet for placement adjacent a body, a liquid impermeable backsheet joined to said topsheet, an absorbent pad disposed between said sheets, front and rear waist areas at opposite ends of the diaper, a leg area intermediate the waist area, a strip of elastic material positioned along each of said side edges in the leg area for providing an elasticized snug fit at the leg area, the improvement wherein a waist area includes an opening in both of the joined sheets, a layer of elastic material is disposed in said opening for providing an elasticized snug fit at the waist area and, at one stage in the fabrication of the diaper, the elastic layer and said elastic strip comprise different portions of the same piece of elastic material.

20. The diaper according to claim 19 wherein, at a later stage in the fabrication of the diaper, said piece of elastic material is discontinuous between said elastic layer and said elastic strip.

* * * * *